United States Patent [19]

Judge

[11] 4,098,576

[45] Jul. 4, 1978

[54] METHOD FOR ANALYZING THE LATENT GAS CONTENT OF METAL SAMPLES

[75] Inventor: James R. Judge, Weirton, W. Va.

[73] Assignee: National Steel Corporation, Pittsburgh, Pa.

[21] Appl. No.: 701,029

[22] Filed: Jun. 29, 1976

[51] Int. Cl.$^2$ .................... G01N 31/10; G01N 31/12
[52] U.S. Cl. ....................... 23/230 PC; 23/253 PC; 73/19
[58] Field of Search ................ 73/19, 23, DIG. 9; 23/230 PC, 232 R, 232 C, 253 PC, 254 R

[56] References Cited

U.S. PATENT DOCUMENTS

| | | | |
|---|---|---|---|
| 3,681,972 | 8/1972 | Mahanty et al. ...................... | 73/19 |
| 3,820,380 | 6/1974 | Miller et al. ........................ | 73/19 |

OTHER PUBLICATIONS

Ichinose, Y.; "A Metallurgical Study of the Production of Fe-Ni Alloys" Chemical Abstracts, vol. 67, No. 6 p. 2315, 8-7-1967.

"Leco Ro-16 Automatic Oxygen Determinator," Laboratory Equip. Corp., pp. 1-3, 7-6-70.

*Primary Examiner*—Richard C. Queisser
*Assistant Examiner*—Stephen A. Kreitman
*Attorney, Agent, or Firm*—Shanley, O'Neil and Baker

[57] ABSTRACT

A method for analyzing the latent gas content of metal samples, particularly the oxygen content of solidified samples of molten steel, which includes charging a crucible in a heat extraction furnace with a metal test specimen and sufficient metallic germanium to cause wetting of the specimen upon heating and disassociation of metallic oxides (or other metallic compounds including latent gaseous constituents) in the test specimen such that gases evolve and are quantitatively measured in conventional apparatus. When a test specimen is analyzed for oxygen content the evolved gas will be principally carbon dioxide, which is usually measured in a gas chromatograph.

19 Claims, No Drawings

METHOD FOR ANALYZING THE LATENT GAS CONTENT OF METAL SAMPLES

BACKGROUND OF THE INVENTION

This invention relates broadly to a method for determining the latent gas content of metal samples and, in particular, to a method for analyzing solidified steel samples to determine their oxygen content.

At various stages during the production of steel it becomes very important to ascertain the oxygen content of the melt in order to determine, for example, the quantity of deoxidizer which must be added at a later stage in the operation. In most cases, the degree of oxidation of the melt is determined by obtaining a sample of the unkilled or semi-killed molten steel, allowing it to solidify, pyrolizing a segment of the solidified sample in a heat extraction furnace, and quantitatively analyzing the effluent gas in an attached gas chromatograph. U.S. Pat. No. 3,820,380 to Miller et al. discusses several analytical methods of this type.

It has been the practice when obtaining such samples to utilize a sampling device including a cavity which contains a killing agent, such as aluminum, zirconium, silicon, or titanium. The killing agent is present in a sufficient quantity to combine with the free oxygen in the molten sample as it fills the cavity so that upon solidification of the sample there will be no substantial loss of oxygen content and no porosity to interfere with the subsequent analysis. Thus, the resulting solidified test ingot contains not only the metallic oxides which may have been originally present in the melt, but also oxidic compounds formed through the reaction of available oxygen and the killing agent. In the ideal situation, such oxides would be completely disassociated upon pyrolysis and the true oxygen content of the sample determined. However, in the past, this ideal has not been realized because of the relatively high melting points of such metallic oxide compounds or because the molecular bonding between the metal and oxygen constituents was strong enough to resist reduction in the absence of a catalyst such as nickel or platinum. Of course, these catalysts could be employed in the procedure but their relatively high costs made their use on a continuing basis economically impractical.

As a result, the prior art procedures frequently produced unreliable analytical data, particularly in relation to the oxygen content of test samples.

SUMMARY OF THE INVENTION

A method has now been discovered for consistently obtaining reliable data concerning the latent gas content of metal samples, and in particular the oxygen content of such samples, which comprises in its broadest sense pyrolizing a test specimen of a metal sample along with a sufficient amount of metallic germanium to wet the specimen and alloy with the specimen so that gaseous elements or compounds evolve which are thereafter quantitatively measured by conventional procedures. The method of this invention is particularly useful in determining the oxygen content of metal samples, the gaseous compounds evolving therefrom primarily comprising carbon dioxide which may be measured, for example, in a standard gas chromatograph. In this connection, this invention may be used not only in determining the oxygen content of a solidified sample of molten steel but it may also be used in determining the oxygen content of various deoxidizers or killing agents themselves as well as refractory materials which may be added to a steel melt in the production of steel. In most instances pyrolysis will be conducted in the inert atmosphere of an induction furnace of any conventional design and the evolved gases measured by standard analytical procedures and devices.

Accordingly, it is a principal object of this invention to provide a consistently reliable method for determining the latent gas content of metal samples.

It is another object of this invention to provide a method for pyrolizing metal samples including metallic oxides therein so as to obtain accurate, reliable data concerning the amount of oxygen within each sample.

It is still another object of this invention to provide a method for determining the oxygen content of a solidified sample of molten steel, and of deoxidizers or refractory materials which may be added in the production of steel.

The accomplishment of these and other objects of the present invention will become apparent in the ensuing detailed description of the invention.

DETAILED DESCRIPTION OF THE PREFERRED EMBODIMENTS

In accordance with this invention the latent gaseous content, and in particular the oxygen content, of metal samples can be reliably determined by pyrolizing a specimen of the sample along with a sufficient amount of metallic germanium to alloy with the specimen and in the presence of carbon form gaseous compounds which are thereafter quantitatively measured by conventional procedures.

Among the metals and metal alloys or compounds which may be analyzed according to this invention are steel, alloys such as STELLITE (a cobalt based alloy) and zirconium, titanium, tungsten, molybdenum, columbium, uranium, and thorium based alloys, and various refractory compounds, such as alumina, which are frequently found in a steel melt.

This invention is particularly useful in steel making operations, where it may be employed in analyzing steel from practically anywhere in the mill, e.g., ingot, bloom, bar, sheet or strip. However, this invention is especially advantageous in determining the oxygen content of solidified samples of molten steel taken at various stages in a steel making process, for example, from the ladle, degasser or mold. A variety of sampling devices are available and may be used for obtaining such solidified samples for analysis according to this invention including, for example, the sampling bomb described in U.S. Pat. No. 3,704,621 to Zickefoose, and the suction sampler described in U.S. Pat. No. 3,915,014 to Judge et al. Each such sampling device includes a cavity for receiving molten steel and a sufficient amount of a killing material, such as titanium, aluminum, silicon or zirconium, to alloy with and kill the steel as it fills the cavity. This killing of the steel is necessary in order to tie up free oxygen therein and to produce a sample which is free of cracks, voids, gas pockets or other imperfections. The sample obtained by such devices may be taken from a molten steel heat of unkilled, semi-killed, capped or even rimmed steel, such as may be contained in any conventional furnace, for example, an open hearth, a BOF furnace or an electric furnace, as well as at other stages in a production operation.

Upon solidification, the sample is treated to remove superficial oxides and impurities from its surface, and a specimen is cut therefrom for subsequent analysis. In the case of a bomb type sample, a disc about one-tenth inch in thickness is machined off the sample at a point between 0.75 and 0.85 inch from the bottom of the ingot and 1 gram test pieces are punched out of this disc for use as test specimens. Where the suction type sampler device is used in which a "lollipop" sample is produced including a pin portion which may be cut by any known means in 1 gram or ½ gram sizes for pyrolysis and subsequent analysis.

A variety of pyrolyzing furnaces are available for use in connection with this invention, including a vacuum heat extraction furnace such as described in U.S. Pat. No. 2,336,075 to Derge. However, a preferred analytical apparatus will include an induction furnace and attached chromatographic analyzer, such as manufactured by Laboratory Equipment Corporation and sold as a LECO Oxygen Determinator. This Determinator consists of an inert gas purification system, a high frequency induction furnace and a gas chromatograph for measuring carbon dioxide. In operating such an apparatus according to this invention, a test specimen is placed in a graphite crucible (fixed between water-cooled electrodes) along with a sufficient amount of metallic germanium to wet the specimen upon heating, cause complete disassociation of the metal oxides in the specimen and, ultimately, the formation of gaseous compounds, principally comprising carbon dioxide. For example, where titanium is used as a deoxidizer in obtaining a sample of molten steel, the ratio of germanium to the deoxidant will at least be within the range of 3 to 1, preferably 3 – 7.5 to 1. Although using an amount of germanium in excess of the ratio 7.5 to 1 does not detrimentally affect the analysis, it is obviously economically impractical. Of course, since the amount of such titanium, or other metallic element used in the sampler as a killing agent is known, the specific amount of germanium needed to establish the appropriate ratio may be easily determined.

As used in this specification the term "wet" or "wetting" signifies a condition wherein a relatively low melting metal, i.e., germanium, becomes fluid upon heating and coats a test specimen having a higher melting point whereupon fusion occurs and the melting point of the refractory materials in the specimen is lowered. Such a wetting condition is especially advantageous where the heating is conducted in a nitrogen atmosphere since it prevents the formation of metal nitrides, e.g., titanium nitride.

Where the sample is obtained in a device utilizing a conventional "getter" or killing agent, such as titanium, the total requirements of germanium obviously must be added to the crucible. However, where, as in a preferred situation, the sampling device includes germanium as a deoxidizer, such as that described in copending application Ser. No. 653,911, filed Jan. 30, 1976 in the name of James R. Judge, now U.S. Pat. No. 4,067,242, the additional germanium added to the crucible will only be that necessary to establish the above ratio. Since the amount of germanium used in the sampling device is known, the amount of that element present in the specimen selected for analysis may be easily determined by known means. In any event, when the appropriate germanium-specimen charge is placed in the graphite crucible, the crucible is then mounted in a quartz thimble and placed in a reactor tube in the induction furnace. An inert carrier gas, preferably helium or argon, is introduced into the furnace at a pressure of approximately 1 kilogram/cm² and a flow rate of 2 l/min. whereupon the furnace is heated to a temperature in excess of 2000° C., usually about 2760° C., but in any event, above the melting point of the germanium-specimen charge.

Upon reaching the desired temperature, the germanium and metal specimen will alloy and pyrolysis occurs as illustrated in the following equations in which titanium dioxide is presumed to exist in the specimen.

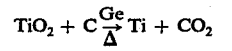

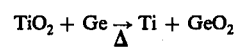

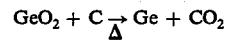

Thus, the germanium acts both as a catalyst and as a reactant in forming an intermediate compound, $GeO_2$. Its catalytic action assists the disassociation of the oxygen constituents from the titanium, permitting the reaction of the free oxygen with carbon from the graphite crucible and, ultimately, the formation of carbon dioxide. Where the germanium itself reacts with the titanium dioxide to produce titanium and germanium dioxide, the germanium dioxide will in turn disassociate in the presence of the carbon to form germanium metal and carbon dioxide. Similar reactions occur when other metallic oxides are present in the test specimen.

As the carbon dioxide evolves from the reaction it is swept from the furnace area by the inert carrier gas through an intermediate catalytic furnace and into a direct reading analyzer unit where it is measured by thermal conductivity. The catalytic furnace contains a bed of copper oxide which oxidizes any residual carbon monoxide in the gas stream to carbon dioxide. Within the analyzer unit the carrier gas transports the carbon dioxide into a trap of molecular sieve at room temperature where adsorption occurs. At the end of a one minute collection time the trap is automatically heated to release the carbon dioxide and solenoid valves simultaneously divert the carrier gas flowing from the furnace to exhaust. A second, separate, carrier stream of purified inert gas, maintained at a pressure of 1.5 Kg/cm² and a flow rate of 200 cc/min., is first passed over a reference thermistor and then directed into the trap so that it sweeps the trap and carries the evolved carbon dioxide through a short silica gel column to a second measuring thermistor. The two thermistors measure thermal conductivity of the respective gas streams and the difference is amplified, integrated and read on a Digital Voltmeter as micrograms of oxygen.

The following example will further illustrate the advantages of the invention. Unless indicated otherwise, all proportions and quantities of materials indicated in the specification should be interpreted as being expressed on a weight basis.

EXAMPLE 0.02 gram of pure $Al_2O_3$ was placed in a graphite crucible adapted for use in a LECO Oxygen Determinator apparatus along with a 1 gram steel test specimen containing a known quantity of oxygen, i.e., 63 ppm of oxygen. The graphite crucible was then mounted within the induction furnace of a LECO Determinator apparatus and bathed in a nitrogen gas atmosphere. The temperature of the furnace was raised to 5000° F. and maintained at that temperature for about 1 minute whereupon the gases evolved from the pyrolysis of the crucible's charge were swept from the furnace into a connection gas chromatograph device wherein the oxygen content was determined in the manner previously indicated. This procedure was repeated four times in order to promote complete disassociation of the metallic oxides in the crucible. Each time a reading was obtained for oxygen content resulting in a total accumulative oxygen readout of 1,660 ppm.

A second experiment was performed in which the graphite crucible was charged with the same amount of $Al_2O_3$ and an identical steel test specimen, i.e., including 63 ppm of oxygen, except in this case 0.15 gram of oxygen-free germanium was also added to the crucible. The same procedure was followed as described above, including five consecutive heatings to 5000° F., as a result of which a total accumulated oxygen content of 3696 ppm of oxygen was indicated by the analyzer.

The obvious conclusion which must be drawn from these experiments is that a more complete disassociation of the $Al_2O_3$ was achieved in the experiment including germanium wherein a more accurate reading of the oxygen content of the heated material was obtained.

The same comparative results will be found in testing any metal specimen, including a solidified sample of molten steel.

The above embodiments are to be considered in all respects as illustrative and not restrictive since the invention may be embodied in other specific forms without departing from its spirit or essential characteristics. Therefore, the scope of the invention is indicated by the claims rather than by the foregoing description, and all changes which come within the meaning and range of the equivalents of the claims are intended to be embraced therein.

I claim:

1. A method for determining the latent gas content of a metal sample which comprises charging a crucible with a metal specimen taken from the sample and a sufficient amount of metallic germanium to wet and alloy with the metal specimen upon heating, pyrolyzing the contents of the crucible in the presence of carbon so as to induce substantially complete disassociation of compounds having metal and latent gaseous constituents within the sample, and to produce the formation and release from the metal specimen of gaseous carbonaceous compounds, collecting and analyzing said gaseous carbonaceous compounds.

2. The method of claim 1 wherein the test specimen contains metal oxides and a major proportion of the evolved gaseous carbonaceous compounds is carbon dioxide.

3. The method of claim 2 wherein the test specimen is taken from a solidified sample of molten steel.

4. The method of claim 2 wherein the metal oxides are of the group consisting of titanium, silicon, zirconium and aluminum oxides.

5. The method of claim 4 wherein the metal oxide is titanium oxide and the weight ratio of germanium to the test specimen is about 3 – 7.5 to 1.

6. A method for determining the oxygen content of metal samples which includes charging a graphite crucible with a metal test specimen and a sufficient amount of metallic germanium to alloy with the test specimen and cause substantially complete disassociation of metallic oxides contained in the specimen upon heating, heating the graphite crucible in an inert gas atmosphere to a temperature above the melting point of the germanium-test specimen charge whereby gaseous carbon-oxygen compounds are formed, collecting the evolved gaseous compounds and analyzing the gaseous compounds for oxygen content.

7. The method of claim 6 wherein the evolved gaseous carbon-oxygen compound is carbon dioxide.

8. The method of claim 6 wherein the metal oxides are included in the group consisting of titanium, silicon, zirconium, and aluminum oxides.

9. The method of claim 8 wherein the metal oxide is titanium oxide and the weight ratio of germanium to test specimen is 3 – 7.5 to 1.

10. The method of claim 6 wherein the heating of the graphite crucible is conducted in an induction furnace and the temperature is raised to a point in excess of 2000° C.

11. The method of claim 6 wherein the inert gas is selected from nitrogen, argon and helium.

12. A method as defined in claim 6 wherein the metal sample is a solidified sample of molten steel.

13. A method for determining the oxygen content of a solidified sample of molten steel comprising, charging a graphite crucible with a test specimen of the solidified sample, and a sufficient amount of metallic germanium to wet and alloy with the test specimen and cause substantially complete disassociation of metallic oxides contained in the specimen upon heating, inductively heating the graphite crucible in an inert gas atmosphere to a temperature above the melting point of the germanium and the test specimen whereby gaseous carbon-oxygen compounds are formed, collecting the evolved gaseous compounds and analyzing the gaseous compounds for oxygen content.

14. The method of claim 13 wherein the evolved gaseous carbon-oxygen compound is carbon dioxide.

15. The method of claim 13 wherein the metal oxides are included in the group consisting of titanium, silicon, zirconium, aluminum and germanic oxides.

16. The method of claim 15 wherein the metal oxide is titanium oxide and the weight ratio of germanium to said oxide is 3 – 7.5 to 1.

17. The method of claim 13 wherein the graphite crucible is heated to a temperature of about 2760° C.

18. The method of claim 13 wherein the inert gas is selected from nitrogen, argon and helium.

19. A method for determining the oxygen content of a solidified sample of molten steel comprising, charging a graphite crucible with (a) a test specimen of the solidified sample, and (b) a sufficient amount of metallic germanium to wet and alloy with the test specimen and cause substantially complete disassociation of metallic oxides contained in the specimen upon heating, heating the graphite crucible in an inert gas atmosphere within an induction furnace to a temperature of about 2760° C. such that the oxygen constituents of the metallic oxides are liberated and form carbon dioxide, purging the carbon dioxide from the furnace to a chromatographic analyzer and, analyzing the carbon dioxide for oxygen content.

* * * * *